US006462089B1

(12) United States Patent
Battaglia et al.

(10) Patent No.: US 6,462,089 B1
(45) Date of Patent: Oct. 8, 2002

(54) METHOD FOR CORRECTING THE VIGILANCE DISORDERS ASSOCIATED WITH MYOPATHIES

(75) Inventors: Fabrice Battaglia, Mulhouse; Jean Krieger; Christophe Petiau, both of Strasbourg; Christophe Vial; Helene Bastuji, both of Lyons; Serge Lubin, Villejuif, all of (FR)

(73) Assignee: Laboratoire L. Lafon, Maisons Alfort (FR)

( * ) Notice: Subject to any disclaimer, the term of this patent is extended or adjusted under 35 U.S.C. 154(b) by 0 days.

(21) Appl. No.: 09/606,238

(22) Filed: Jun. 29, 2000

(30) Foreign Application Priority Data

Jan. 31, 2000 (FR) .............................. 00 01211

(51) Int. Cl.$^7$ ........................................... A61K 31/165
(52) U.S. Cl. ....................... 514/618; 514/923
(58) Field of Search ................. 514/618, 923

(56) References Cited

U.S. PATENT DOCUMENTS 5,618,845 A * 4/1997 Grebow et al. ............. 514/618

FOREIGN PATENT DOCUMENTS

| EP | 0 233 106 | 8/1987 |
| FR | 2 385 693 | 10/1978 |

OTHER PUBLICATIONS

Chemical Abstract 126:258987, "Selegiline in the treatment of hypersomnolence in mytotonic dystrophy: a pilot study" (1997).*

Marchand, F. et al, "Therapeutic results of modafinil in 32 patients out of 112 hypersomniacs examined in a sleep unit", Neurophysiol. Clin., vol. 21, No. 3, 1991, p. 227.

Petiau, C. et al, "Somnolence diurne pathologique", Revue de Medecine Interne, vol. 18, No. 3, 1997, pp. 210–218.

Bastuji, H. et al, "Successful Treatment of Idiopathic hypersomnia and narcolepsy with modafinil", Progress in Neuro–Psychopharmacology and Biological Psychiatry, vol. 12, No. 5, 1988, pp. 695–700.

Rochegude, S. et al, "Le modafinil: Modiodal®". Lyon Pharmaceutique, vol. 27, No. 7, 1996, pp. 363–366.

Schwartz, J. et al, "Modafinil for the Treatment of Excessive Daytime Sleepiness Associated with Narcolepsy", Today's Therapeutic Trends, vol. 16, No. 4, 1998, pp. 287–308.

Beusterien, K. et al, "Health–Related Quality of Life Effects of Modafinil for Treatment of Narcolepsy", Sleep, vol. 22, No. 6, Sep. 15, 1999, pp. 757–765.

Billiard, M. et al, "Modafinil: A Double–Blind Multicentric Study", Sleep, vol. 17, No. Suppl. 8, 1994, pp. S107–S112.

Billiard, M., "Narcolepsie", Revue du Praticien, vol. 46, No. 20, Dec. 15, 1996, pp. 2428–2434.

Arnulf, I. et al, "Modafinil in Obstructive Sleep Apnea–Hypopnea Syndrome: A Pilot Study in 6 Patients", Respiration, vol. 64, No. 2, 1997, pp. 159–161.

* cited by examiner

*Primary Examiner*—Frederick Krass
(74) *Attorney, Agent, or Firm*—Jacobson Holman, PLLC

(57) ABSTRACT

The present invention relates to the use of modafinil and isomers thereof for correcting psychosocial life disturbances due to vigilance disorders observed during the evolution of myopathies.

11 Claims, No Drawings

METHOD FOR CORRECTING THE VIGILANCE DISORDERS ASSOCIATED WITH MYOPATHIES

The present invention relates to a novel therapeutic use of modafinil and derivatives thereof.

Modafinil, or benzhydrylsulphinylacetamide, is a compound of formula:

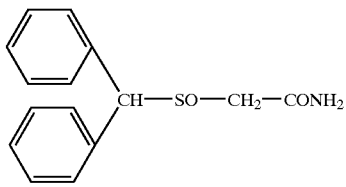

This compound and its therapeutic use as an active agent on the central nervous system have been described in patent application FR-A-2,385,693.

Modafinil is used therapeutically in the treatment of narcolepsies and idiopathic hypersomnias.

The laevorotatory and dextrotatory isomers of modafinil have also been described in EP-A-0 233 106, the laevorotatory isomer being presented as having better bioavailability.

It has now been discovered that modafinil and the isomers thereof have a beneficial effect on the vigilance disorders associated with myopathies and in particular with myotonic dystrophy.

Myotonic dystrophy, or Steinert's disease, which is the most frequent of the adult dystrophies, is a hereditary disease whose prevalence is estimated to be about 5 to 8/100,000 (P. S. Harper, in "Myotonic dystrophy", $2^{nd}$ Ed., Saunders, Pa., USA, 1989). This disorder, which is transmitted according to a dominant autosomal method, is always associated with a genetic abnormality (located on chromosome 19) which is characterized by an abnormal amplification of a trinucleotide sequence belonging to a gene encoding a protein kinase.

Myotonic dystrophy is a multisystem pathology which can include an attack of the skeletal and respiratory muscles, of the heart, of the endocrine system, of the lens of the eye and of the central nervous system. It is often revealed by the musculo-skeletal attack which comprises a spontaneous or provoked myotony, an atrophy and a motor deficiency which essentially affects the muscles of the face, the muscles for chewing, the sterno-cleido-mastoid muscles and the distal musculature of the limbs. The neurological attack (objectified by MRI) comprises lesions such as ventricular dilation, atrophy and modification of the subcortical white matter, as well as hippocampal neurofibrillar degenerations and neuronal losses. This neurological attack is revealed, clinically speaking, by cognitive disorders which can range up to an overall picture of subcortical dementia, a lack of initiative and personality disorders (indifference, laziness, aggressiveness, etc.).

An effect on respiratory function and sleep disorders are common. For some patients, the principal discomfort expressed is severe diurnal hypersomnolence (P. S. Harper, R. Rüdel, in "Myotonic Dystrophy", A. Engel and C. Franzini-Armstrong, eds. Myology $2^{nd}$ Edition, 1994). The mechanisms of the diurnal hypersomnia of myotonic dystrophy are still unknown. It might be related to a carbonarcosis linked to an alveolar hyperventilation, or to a syndrome of sleep apnoea which are central and/or obstructive or of idiopathic origin. However, diurnal hypersomnia episodes can be observed in dystrophic patients who have a functional respiratory examination assessment which is normal and a polysomnography which is also normal. In this situation, Steinert's myotonic dystrophy would result from an attack of the central nervous system, which is not evoked in the conventional overall pictures of Gélineau disease (narcolepsy), sleep apnoea or idiopathic hypersomnia (Van der Meché et al., Neurol, Neurosurg Psychiatry, 57: 626–628, 1994; Ono et al., Neurology, 46: 228–231, 1986).

The diurnal hypersomnolence of patients suffering from Steinert's disease (myotonic dystrophy) has already been the subject of a number of therapeutic attempts using medicinal products which have stimulatory properties on the central nervous system.

The medical literature available to date presents preliminary results obtained with two compounds which have different mechanisms of action and pharmacological profiles: methylphenidate (Van der Meché et al., Muscle and Nerve 9: 341–344, 1986) and selegiline (Antonini et al., J. Neurol. Sciences 147; 167–169, 1997). In the first case, an improvement in the level of consciousness was observed, whereas the use of the monoamine oxidase MOA-B inhibitor proved to be ineffective at the dose of 20 mg/day.

This context of therapeutic attempts, which is relatively unfavourable, can perhaps be linked to the physiopathological specificity of myotonic dystrophy, especially when it is accompanied by CNS lesions which are found neither in Gélineau disease nor in idiopathic hypersomnias nor in sleep apnoea.

Modafinil differs considerably from the conventional psychostimulants (d-amphetamine, methylphenidate) with respect to neurochemlical activity. Specifically, within the dose ranges which modify consciousness, modafinil, unlike d-amphetamine and methylphenidate, has no effect on dopamine, which is the principal target of the conventional psychostimulants. Modafinil also differs from amphetamine in terms of behavioural activity. In addictive substance discrimination tests, the generalization of the effects of modafinil with amphetamine is very weak; modafinil leads neither to self-administration nor to preference of place, which are two behaviours rapidly developed in the case of conventional psychostimulants. In addition, modafinil does not modify the self-administration of cocaine and does not influence the relapse of this behaviour. Finally, while modafinil can activate the expression of the c-fos proto-oncogene in cerebral tissue, it does so in zones which are entirely different from those with which the conventional psychostimulants are concerned. Thus, in a publication by J S. Lin et al. (PNAS, 1996), the c-fos proto-oncogene is not expressed in the central dopaminergic projection zones (including the cortex) after administration of awakening doses of modafinil in cats, whereas it is highly expressed in these regions after administration of equally-awakening doses (with respect to those of modafinil) of d-amphetamine and of methylphenidate.

With these trains of thought and these experimental data in mind, the inventors have discovered, unexpectedly, that modafinil administered to patients suffering from myotonic dystrophy makes it possible to restore a level of diurnal vigilance which is compatible with a satisfactory psychosocial life and relationships. These positive results appear to be all the more unexpected given the fact that patients suffering from Steinert's disease have normal function or respiratory examinations and normal polysomnography assessments, which are situations which are a good argument for an original effect of modafinil which is independent of what has already been discovered and what has been the subject of patents for already adapted therapeutic use.

The inventors have discovered more generally that modafinil and the isomers thereof make it possible to correct the vigilance disorders which are observed during the evolution of myopathies.

A subject of the present invention is thus a method for correcting vigilance disorders observed during the evolution of myopathies in a patient, which comprises the administration to this patient of an effective dose of modafinil or of one of the isomers thereof.

A subject of the present invention is more particularly a method for correcting vigilance disorders associated with myotonic dystrophy, or Steinert's disease, which comprises the administration to this patient of an effective dose of modafinil or of one of the isomers thereof.

In patients suffering from myopathies, and in particular from myotonic dystrophy, modafinil and the isomers thereof can be used to specifically combat diurnal hypersomnolence, in order to restore a sleep pattern which is comparable to that of normal sleep and to improve the quality of psychosocial life and relationships.

Modafinil and the isomers thereof can be administered in a form which is suitable for oral administration, and which contains modafinil or each of the isomers thereof in single doses of between 50 and 600 mg, preferably 100 to 400 mg.

The preferred pharmaceutical forms are pharmaceutical forms intended for repeated oral administration in the form of breakable or unbreakable tablets, gel capsules, wafer capsules or controlled-release microgranules.

Modafinil can, however, be administered via other routes, in particular transdermally, and can be provided in the form of ointments, salves, gels, solutions, lotions, liquid forms which form films on the skin for transdermal administration or forms of "patch" type.

Thus, in a series of patients suffering from myotonic dystrophy, in whom validated methods for studying disturbances of the waking/sleeping cycle had demonstrated diurnal hypersomnias of frequency and duration which were considered to be pathological (with respect to clinical and therapeutic experience of sleep apnoeas and narcolepsy), [patients] were treated with oral doses of modafinil of between 100 and 400 mg/day. In the majority of these patients, the modafinil treatment proved to be subjectively effective; the patients report a clear regression of the vigilance disorders and diurnal somnolence and an improvement of their psychosocial life.

By way of example, in a patient suffering from Steinert's disease, which is characterized, inter alia, by a temporal atrophy, ptosis, a myotony associated with muscle weakness, behavioural disorders and somnolence (the start of which went back to 1988) with sleep paralyses, without hypnogogic hallucinations or attacks of cataplexy, a decrease was observed of 18 units on the Epworth somnolence scale (see Johns M. W. Sleep, 1991, 14, 540) after treatment with an oral dose of 100 mg per day of modafinil for six months, between February 1999 (score on the Epworth scale=20) and August 1999 (score on the Epworth scale=2).

The benefit provided by modafinil was also demonstrated in two other patients suffering from Steinert's disease. The first, of female gender, exhibited the telling morphotype (atrophy of the temporal fossae), as well as a deficiency of the lower limbs, cervical weakness and diffuse myotony. Diurnal hypersomnia was severe, since she had a score of 16 on the Epworth scale before treatment. The effectiveness of modafinil (dose=200 mg/day) revealed itself by an improvement in the somnolence score on the Karolinska KSS scale (Akerstedt P., Gillberg M., Int. J. Neurosci. 1990; 52: 29–37) (before: 8/after: 2) and especially by a considerable improvement in her personal and professional daily life. In the second patient of this series, the telling morphotype and a myotony of both hands associated with muscular deficiency existed. Without treatment, diurnal hypersomnia was very pronounced (Epworth scale: 16). The administration of modafinil (dose=600 mg/day) induced a partial resolution of the diurnal somnolence attacks, since the somnolence score on the Karolinska scale went from 8 to 4.

What is claimed is:

1. Method for restoring a normal sleep pattern and for improving the quality of psychosocial life and relationships in a patient suffering from a myopathy which comprises administration to the patient of an effective amount of a compound selected from the group consisting of modafinil and the isomers thereof.

2. Method of claim 1 wherein the myopathy is myotonic dystrophy.

3. Method for correcting vigilance disorders observed in a patient suffering from a myopathy, which comprises administration to the patient of an effective amount of a compound selected from the group consisting of modafinil and the isomers thereof.

4. Method for correcting vigilance disorders in a patient suffering from myotonic dystrophy, or Steinert's disease, which comprises administration to the patient of an effective amount of a compound selected from the group consisting of modafinil and the isomers thereof.

5. Method for treating diurnal hypersomnolence in a patient suffering from a myopathy, which comprises administration to the patient of an effective amount of a compound selected from the group consisting of modafinil and the isomers thereof.

6. Method of claim 5, wherein the myopathy is myotonic dystrophy.

7. Method according to claim 1, which comprises oral administration of modafinil in unit doses of between 50 and 600 mg.

8. Method according to claim 7, which comprises repeated oral administration of modafinil in the form of breakable or unbreakable tablets, gel capsules, wafer capsules, or controlled-speed microgranules.

9. Method according to claim 3, which comprises oral administration of modafinil in unit doses of between 50 and 600 mg.

10. Method according to claim 4, which comprises oral administration of modafinil in unit doses of between 50 and 600 mg.

11. Method according to claim 5, which comprises oral administration of modafinil in unit doses of between 50 and 600 mg.

* * * * *